United States Patent
McLeod et al.

(10) Patent No.: US 7,236,818 B2
(45) Date of Patent: Jun. 26, 2007

(54) HANDHELD INTERPRETING ELECTROCARDIOGRAPH

(75) Inventors: Michael P. McLeod, Grafton, WI (US); Richard Bechtel, Dousman, WI (US); Robert Michalski, West Bend, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 251 days.

(21) Appl. No.: 09/976,538

(22) Filed: Oct. 12, 2001

(65) Prior Publication Data
US 2003/0073915 A1 Apr. 17, 2003

(51) Int. Cl.
*A61B 5/0404* (2006.01)

(52) U.S. Cl. .......................... 600/509; 128/903; 607/30

(58) Field of Classification Search ................ 600/508, 600/509, 521, 523, 525; 128/903; 607/4, 607/5, 9, 30, 32
See application file for complete search history.

(56) References Cited

U.S. PATENT DOCUMENTS

| | | | | |
|---|---|---|---|---|
| 5,782,773 A | * | 7/1998 | Kuo et al. ................. 600/523 |
| 5,873,838 A | * | 2/1999 | Mogi ......................... 600/509 |
| 5,876,351 A | * | 3/1999 | Rohde ........................ 600/523 |
| 5,891,045 A | * | 4/1999 | Albrecht et al. ............ 600/509 |
| 5,899,855 A | * | 5/1999 | Brown ....................... 600/301 |
| 6,141,584 A | * | 10/2000 | Rockwell et al. .............. 607/5 |
| 6,292,692 B1 | * | 9/2001 | Skelton et al. ................. 607/5 |
| 6,603,995 B1 | * | 8/2003 | Carter ........................ 600/509 |
| 6,654,631 B1 | * | 11/2003 | Sahai ......................... 600/509 |
| 6,730,025 B1 | * | 5/2004 | Platt .......................... 600/300 |
| 6,754,355 B2 | * | 6/2004 | Stetzler et al. ............. 381/94.2 |
| 6,773,396 B2 | * | 8/2004 | Flach et al. ................. 600/300 |

* cited by examiner

*Primary Examiner*—Carl Layno
*Assistant Examiner*—Frances P. Oropeza
(74) *Attorney, Agent, or Firm*—Welsh & Katz, Ltd.

(57) ABSTRACT

A hand-held electrocardiograph system with automatic analysis and interpretation is provided. The electrocardiograph includes an acquisition element adapted to be coupled to a patient through a set of relatively short leadwires and a hand-held, battery powered portable processing and display element coupled to the acquisition element and controlled through a graphical user interface.

14 Claims, 4 Drawing Sheets

HANDHELD INTERPRETING ELECTROCARDIOGRAPH

FIELD OF THE INVENTION

The field of the invention relates to cardiac monitoring and more particularly to electrocardiographs.

BACKGROUND OF THE INVENTION

Electrocardiograms are typically generated by an electrocardiograph under a 12-lead format. Cardiac signals detected among the leads of the electrocardiograph are typically no more than a few millivolts in magnitude.

The generation of electrocardiograms is subject to a number of difficulties. For example, the heart is a relatively small muscle compared to other muscles of the body. As a consequence, cardiac signals may be overwhelmed by signals generated by other muscles or by noise in general.

Electrocardiograms are typically generated on a moving paper strip using a pen for each lead. In the case of a 12-lead electrocardiogram 12 pens are required. Because of the number of signals, prior art electrocardiographs have generally been relatively large with limited mobility. The limited mobility of electrocardiographs has generally limited their usefulness to hospitals and ambulances. Because of the importance of cardiac monitoring, a need exists for more mobile electrocardiographs.

SUMMARY

A hand-held electrocardiograph system with automatic analysis and interpretation is provided. The electrocardiograph includes an acquisition element adapted to be coupled to a patient through a set of relatively short leadwires and a hand-held, battery powered portable processing and display element coupled to the acquisition element and controlled through a graphical user interface.

DETAILED DESCRIPTION OF A PREFERRED EMBODIMENT

Figure 1:
FIG. 1 depicts an electrocardiograph system shown in a context of use.

FIG. 1 is a block diagram of an electrocardiograph system 10, shown generally under an illustrated embodiment of the invention in a context of use. Included within the system 10 is an acquisition unit 12 and a processing and display unit 14. A connector cable 50 may be used to couple the acquisition unit 12 to the display unit 14.

A set of leadwires 16 is provided to connect the system 10 to a body of the patient. A patient connector block assembly 18 is provided to detachably couple each leadwire in the set of leadwires 16 to the acquisition unit. The system 10 has been found to offer compliance with applicable medical safety and performance standards (e.g., IEC601-1, AAMI EC11, etc.) and superior performance over prior art devices for a number of reasons. For example, fabrication of the system 10 as a two part unit allows the acquisition unit 12 to be placed directly on (or near) the chest of the patient, thereby greatly reducing the length of the leadwires 16. Reducing the length of the leadwires has been found to significantly reduce the incidence of electromagnetic interference (EMI). Further, by separating the acquisition function from the processing and display function, the acquisition unit 12 may be made smaller and used more comfortably in closer proximity to the body of the patient.

The display unit 14 (and acquisition unit 12) may be provided as a handheld, battery powered device with an integral display 20 substantially covering a top portion of the display unit 14. The display 20 may be provided with a graphical-user-interface (GUI) to further reduce the size of the display unit 14.

It should be understood that any configuration may be used with regard to processing of cardiac signals derived from the leadwires 16. For example, for a standard 12-lead ECG, only 8 leads (e.g., I, II, and V1 through V6) may be physically present. The remaining 4 leads may be derived via Einthoven's law (as recommended by the American Heart Association).

Figure 2:
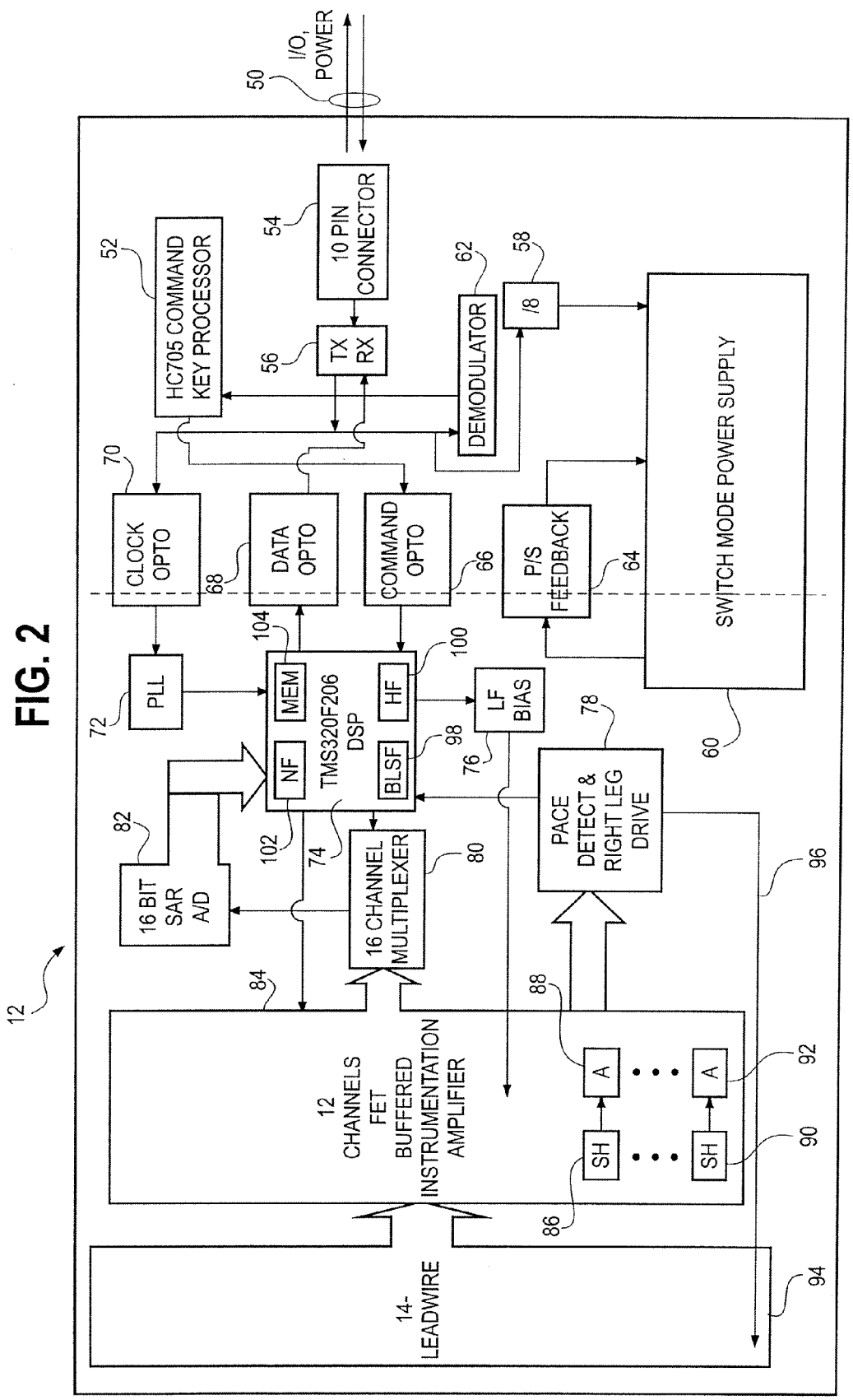
FIG. 2 is a block diagram of an acquisition unit used with the system of FIG. 1.

Returning now to the acquisition unit 12, FIG. 2 is a block diagram that may be used to depict the functionality of the acquisition unit 12. As shown, a patient connector block 94 may be used to receive patient leadwires 16. Cardiac signals may be coupled through the leadwires 16 and connector block 94 to a respective channel of a programmable amplifier 84.

Within the amplifier 84, the signal of each channel may be coupled to a respective amplifier 88, 92. The Analog to Digital converter (ADC) 82 may simultaneously collect samples at 4,000 samples per second (sps) under control of a digital signal processor (DSP) 74. A reference connection (e.g., connected to the right leg of the patient) 96 may be used to reduce common mode noise by providing a signal reference for each difference amplifier 200. A lead fail bias circuit 76 may provide an amplification programming signal to each of the programmable amplifiers 88, 92.

The amplified signals of the respective leadwires 16 may be amplified within a portion of the amplifiers 88, 92 and provided as an input to an analog multiplexer 80. The multiplexer 80 may sequentially couple an output of each amplifier 88, 92 to an analog to digital converter (ADC) 82.

Within the ADC 82, the analog signal of each lead is converted into a digital representation of the signal. The digitized signals, in turn, are transferred to the DSP 74. From the DSP 74, the digitized data may be transferred through an optical coupler 68 to a communication processor 56. From the communication processor 56, the signals may be transferred through a connector 54 and cable 50 to the display unit 14.

In addition to acting as a destination for cardiac signals, the display unit 14 may also serve as a source for command and control signals for signal acquisition and, more specifically, for control of the DSP 74. As an example, the display unit 14 may download filtering parameters used by the DSP 74 in rejecting noise.

In general, information downloaded from the processor 14 may be passed to a demodulator 62 where the transmitted information may be recovered. From the demodulator 62, the information is transferred to a command key processor 52 where the downloaded information may be formatted into a form understood by the DSP 74. From the command key processor 52, the information may be transferred through an optical interface 66 directly to the DSP 74 for execution.

The division of processing responsibilities between the acquisition unit 12 and display unit 14 functions to improve the overall performance of the system 10 by allowing for specialized processors to be dedicated to specific tasks. For example, the DSP 74 may be chosen to be specifically adept at filtering, while the CPU 30 of the processor 14 may be chosen for display capabilities. The DSP 74 may also be chosen to simply collect raw data samples and perform no filtering, while the CPU 30 of the processor 14 performs all the filtering, data analysis and display capabilities.

In general, three different types of noise may be accommodated within the system 10. Noise may arrive via the power supply or from fluorescent lights. A notch filter processor 102 within the DSP 74 may be used to substantially eliminate power supply noise from the acquired signal. To suppress power supply noise, a set of filter parameters may be downloaded to the noise filter processor 102 upon startup for a specific power source frequency (e.g., 50 Hz, 60 Hz, etc.).

Alternatively, low and high frequency noise may be processed and removed. Low frequency noise may result from patient respiration or the slowly changing potentials caused by the electrode-electrolyte-skin interface. This may be referred to by the term "baseline sway", which generally occurs at less than 1 Hz in the signal frequency spectrum.

A baseline sway filter (BLSF) 98 may function to reduce baseline sway. In general, the BLSF 98 may be programmed to operate at any appropriate roll-off point (e.g., 0.01 Hz, 0.02 Hz, 0.16 Hz, 0.32 Hz, 0.64 Hz, etc.). Filter parameters may be selected and downloaded from the display 14 unless filters are performed by the CPU in the display element.

In general, the higher the setting of the BLSF 98, the more aggressively the filter smoothes out a wandering baseline. The digital filter 98 functions by subtracting a portion of the difference between a signal and its mid-channel potential. The longer the signal strays away from its midpoint, the greater the portion of the difference that may be subtracted. The result of the processing is that it removes baseline sway. However, a higher frequency waveform (i.e., caused by the QRS complex) is not significantly altered.

A high frequency filter (HF) processor 100 may be used to remove high frequency noise. However, muscle tremor may have some of the same high frequency characteristics of the relatively small high frequency components of the ECG. For example, where a high frequency roll-off point of 40 Hz is selected, the ECG may be distorted because it also removes ECG signal components with frequencies greater than 40 Hz. To avoid distortion, a roll-off frequency of 150 Hz may be selected for the HF processor 100.

As a further feature, a multi-lead pace detector 78 may be provided which functions to identify spikes indicative of pacemaker operation based upon a pacer algorithm. The algorithm identifies pacemaker artifacts by finding either large amplitude spikes (e.g., greater than 1000 millivolts) or lower amplitude spikes (e.g., greater than 250 microvolts) having predetermined pulse characteristics (e.g., high rate of rise, narrow width, etc.). The pace detector 78 may function to store pacing spikes along with a relative time of occurrence within the ECG.

In addition to downloaded commands, the processor 14 may also provide a reference clock frequency. The reference clock frequency may be provided at a lower frequency, which may be passed through an optical interface 70 to a phase-locked-loop (PLL) 72. The PLL 72 may synchronize a relatively high frequency internal clock of the DSP 74 to the reference clock from the display 14.

Figure 3:
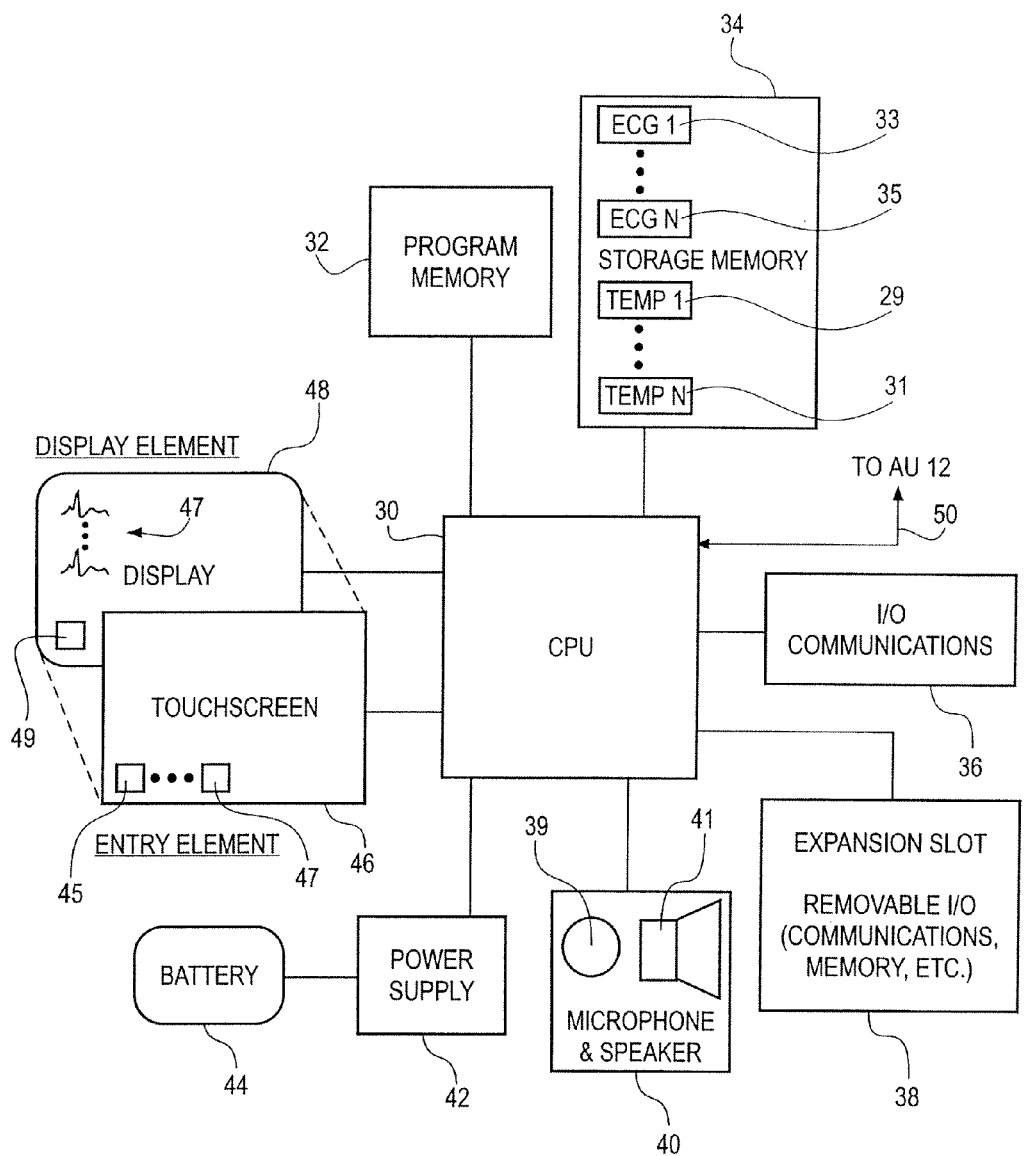
FIG. 3 is a block diagram of a processing unit used with the system of FIG. 1.

Turning now to the display 14, FIG. 3 is a block diagram depicting functional elements of the display 14. A battery (e.g., alkaline, lithium ion, etc.) 44 may provide power to a power supply 42. The power supply 42, in turn, may supply and control a switch-mode power supply 60 within the acquisition unit 12.

Under illustrated embodiments of the invention, sampled data may be filtered within the acquisition unit 12 and then uploaded from the acquisition unit 12 to the display unit 14 for display, storage or transfer to other information processing devices (not shown). The display unit may be any color graphical, liquid crystal display with sufficient resolution (e.g., 640×480 pixels) for waveform display.

The display unit 14 may be based upon any appropriately featured processing platform (e.g., a personal digital assistant (PDA)). To facilitate ease of use of the display unit 14, the CPU 30 may operate under a windows-based environment (e.g., WinCE). A GUI 46 may be provided for control of system functions. By providing a GUI 46, it is contemplated that very few mechanical switches (other than OFF-ON) would be required for control of the system 10.

Upon activation (or during normal operation) of the system 10, the display 48 may include a MENU softkey 49. Activation of the MENU softkey 49 may cause the GUI 46 to occupy at least a portion of the display 48. Contained within the GUI 46 may be a number of softkeys 45, 47 for control and operation of the system 10.

Figure 4:
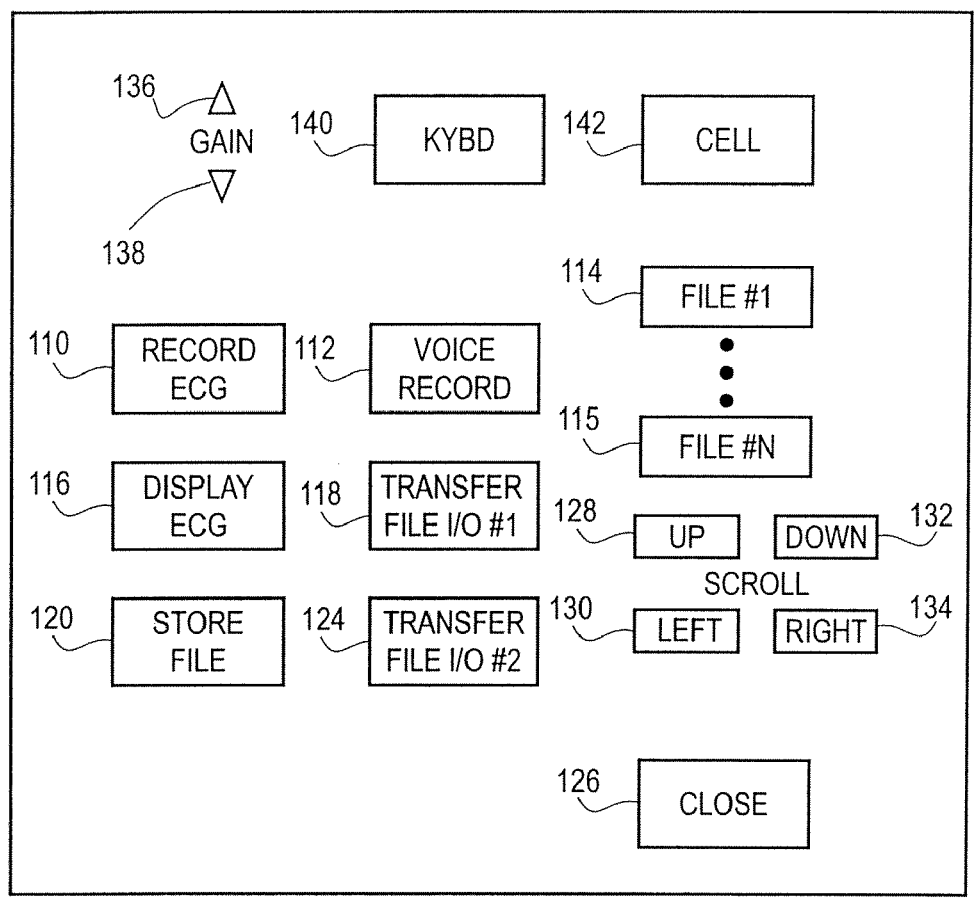
FIG. 4 depicts a graphical user interface that may be used with the system of FIG. 1.

FIG. 4 provides an example of the softkeys that may be included within the GUI 46. Upon opening the GUI 46, the user may select an appropriate function and then close the GUI 46 using the CLOSE softkey 126.

For example, the user may select a softkey 116 labeled DISPLAY ECG and be able to review cardiac activity in real time. In response, the acquisition unit 12 collects and the display unit 14 displays a continuous stream of cardiac data.

While viewing the data, the user may again access the MENU 49 to adjust a gain of the displayed cardiac data. Up and down keys 136, 138 may be provided to ensure sufficient range in the displayed data.

Alternatively, the user may select RECORD ECG 110 to initiate collection of a finite duration, such as 10 seconds, of cardiac activity for display of an electrocardiogram. In response, the acquisition unit 12 may collect 10 seconds worth of data and may upload the data to the display unit 14.

When uploaded, the display unit 14 may display the data as received, or it may perform further data conditioning. While the following description will assume that the CPU 30 of the display unit 14 performs the data conditioning, it should be understood that any portion of the data conditioning could also be performed by the DSP 74.

As a first step, the CPU 30 may operate to identify the QRS complexes within the 10 seconds of acquired raw ECG data. To identify the QRS complexes, the CPU 30 may sum a pre-processed output of all the leads (leads are mathematically derived from the combination of leadwires). Two threshold values may be used. A first lower level may be used to detect the QRS-T complex. A second, higher threshold level may be used to detect the RS portion of the QRS complex.

Once the QRS complex is identified, the CPU 30 may form a template of the QRS complex for each lead. Once a template is formed for each lead, the CPU 30 may move through the 10 seconds of data looking for the same shape on each lead. If it finds a match, the CPU 30 classifies it as another QRS detection. The template may be slid back and forth across likely waveforms to optimize the precise location of detected QRS complexes.

Before further signal processing, the CPU 30 may determine which beat type predominates for later morphology measurements. The CPU 30 may use RR intervals (i.e., the time interval between corresponding R-waves in the successive QRS complexes) and the location of any pacer spikes in order to decide which beat type predominates. Substantially identical QRS shapes may even be subdivided, as in the case of a sinus rhythm with premature atrial beats. A representative cardiac cycle is formed from the data samples of the cardiac cycles with nearly identical QRS shapes. The representative cycle is analyzed to obtain the ECG measurements and detailed shape information and to provide contour interpretation of ECG such as bundle branch blocks, ventricular and atrial hypertrophies, acute myocardial infarction, old myocardial infarction and cardiac ischemia. The raw ECG data and the representative cycle are analyzed to provide detailed rhythm interpretation such as electronic artificial pacing of atria and/or ventricles, atrial flutter, ectopic atrial rhythm, sinus rhythm with or without atrio-ventricular blocks, sinus tachycardia junctional rhythm, atrial fibrillation, etc. Contour interpretation and the rhythm interpretation together constitute the complete ECG interpretation.

At any instant, the operator may select and view waveform data 47. To view the data, the operator may select MENU 49 and DISPLAY ECG 116. To optimize ECG detail, one or more waveforms may be presented on the display 48. A set of scroll softkeys 128, 130, 132, 134 may be provided to view any portion of the ECG.

The operator may also store an ECG in memory 34. When the operator activates a store softkey 120, the CPU 30 may prompt the operator for a patient identifier using a speaker 41 and a prerecorded prompt. The operator may respond into a microphone 39 with a patient name and other descriptive information. The CPU 30 may sample the spoken words and store the descriptive information along with the waveforms within an ECG file 33, 35 stored in memory 34. An icon 114 may be displayed on the GUI 46 to allow recovery of a file 33, 35.

As an alternative to the audio interface, a user may also activate a KYBD softkey 140 and be presented with a keyboard in the GUI 46. Using the keyboard touch screen, the user may type in a patient's name and other distinguishing characteristics.

Alternatively, the user may attach a connector of a laptop-style full travel QWERTY keyboard (not shown) into the expansion slot 38. Entry of data may be made directly through the keyboard.

A communications transceiver (e.g., wireless infrared, radio frequency, or wired RS232, etc.) 36 may be provided. Where a cellular connection is used (e.g., a cellular GSM modem), a CELL softkey 142 may be used to display a keypad (not shown) for entry of a destination telephone number. Where a network connection is used (e.g., wired or wireless local or wide area Ethernet networks), a network softkey may be used to display a keypad (not shown) for entry of a destination network address. Using the communications transceiver 36, the operator may download an ECG to other processing equipment through the transceiver 36 for further analysis by activating a transfer softkey 118.

Alternatively, the operator may store the ECG in removable memory module 38 (e.g., a Flash or Compact Flash Card). Using the removable memory module 38, the operator may store any number of ECGs for later review or transfer to other processing equipment.

Alternatively, the operator may print real time or stored ECG's on an optional printer. The printer may be connected via a communications transceiver (e.g., wireless infrared, radio frequency or wired RS232, etc.).

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A twelve channel electrocardiograph system comprising:
   an acquisition element adapted to be disposed on a chest of a patent, to generate a twelve lead electrocardiograph signal and to be coupled to the patient through a set of relatively short leadwires;
   a hand-held, battery powered portable processing element that is physically separate from the acquisition element and coupled to the acquisition element through a connector cable, said portable processing unit controlled by a central processing unit through a graphical user interface, wherein said central processing unit provides a relatively low frequency reference clock frequency to the acquisition element through the connector cable, wherein said acquisition element further comprising a digital signal processor and an analog-to-digital converter that samples the twelve lead electrocardiogram signal under control of the digital signal processor and a plurality of programmable filters within the digital signal processor specifically adapted to filter the twelve lead electrocardiogram signal from the analog-to-digital converter under control of the central processing unit and wherein said digital signal processor further comprises a relatively high frequency internal clock that is synchronized to the relatively low frequency reference frequency of the central processing unit via a phase-locked loop; and
   a windows operating system within the portable processing element that controls the acquisition element and portable processing element through the graphical user interface.

2. The electrocardiograph system as in claim 1 wherein the processing element further comprises a display.

3. The electrocardiograph system as in claim 2 wherein the display further comprises a liquid crystal display.

4. The electrocardiograph system as in claim 3 wherein the liquid crystal display further comprises a color or monochrome graphical display with sufficient resolution to display waveforms.

5. The electrocardiograph system as in claim 2 wherein the display further comprises a touch screen interface.

6. The electrocardiograph system as in claim 1 wherein the processing element further comprises a compact flash card or similar memory expansion slot.

7. The electrocardiograph system as in claim 6 wherein the compact flash expansion slot further comprises a compact flash read only memory disposed in the compact flash card expansion slot.

8. The electrocardiograph system as in claim 1 wherein the processing element further comprises an infrared transceiver for communications.

9. The electrocardiograph system as in claim 1 wherein the processing element further comprises a radio frequency transceiver for communications.

10. The electrocardiograph system as in claim 1 wherein the processing element further comprises an audio recording unit.

11. The electrocardiograph system as in claim 1 wherein the acquisition element further comprises a plurality of signal conditioning circuits.

12. The electrocardiograph system as in claim 1 wherein the acquisition element further comprises a baseline sway filter.

13. The electrocardiograph system as in claim 1 wherein the acquisition element further comprises a pacemaker pulse detector adapted to detect pacemaker signals.

14. The electrocardiograph system as in claim 1 wherein the acquisition element further comprises analysis and interpretation.

\* \* \* \* \*